United States Patent [19]

Suzuki et al.

[11] Patent Number: 5,225,345
[45] Date of Patent: Jul. 6, 1993

[54] PLANT TISSUE CUTTING AND TRANSPLANTING APPARATUS

[75] Inventors: Akira Suzuki; Hiroyoshi Konno, both of Tokyo, Japan; Robert D. Hartman, Sebring, Fla.

[73] Assignees: Kirin Beer Kabushiki Kaisha; Twyford International Inc., both of Tokyo, Japan

[21] Appl. No.: 733,214

[22] Filed: Jul. 19, 1991

[30] Foreign Application Priority Data

Jul. 23, 1990 [JP] Japan .................................. 2-194196

[51] Int. Cl.$^5$ ......................... C12M 3/00; A01C 11/02
[52] U.S. Cl. .................................... 435/284; 47/1.01; 47/901; 111/200
[58] Field of Search ............... 435/284–287, 435/47, 111; 422/63, 66, 67; 53/448; 100/101, 105; 47/73, 77, 58, 87, 1.01, 901; 111/200, 915, 919; 83/123–146; 425/422

[56] References Cited

U.S. PATENT DOCUMENTS

| | | | |
|---|---|---|---|
| 2,525,987 | 10/1950 | Williamson | 83/127 |
| 3,799,078 | 3/1974 | Blackmore et al. | 47/87 |
| 3,820,480 | 6/1974 | Blackmore et al. | 111/2 |
| 3,903,643 | 9/1975 | Blackmore et al. | 47/77 |
| 4,313,358 | 2/1982 | Brown | 83/127 |
| 4,408,549 | 10/1983 | Qvarnström | 47/58 |
| 4,481,893 | 11/1984 | Qvarnström | 47/58 |
| 4,910,146 | 3/1990 | Tur-Kaspa et al. | 435/284 |
| 4,947,582 | 8/1990 | Visser | 47/1.01 |
| 5,035,105 | 7/1991 | Qvarnström | 53/247 |
| 5,048,434 | 9/1991 | Forster et al. | 47/901 |

FOREIGN PATENT DOCUMENTS 0232628 8/1987 European Pat. Off. .
0389019 9/1990 European Pat. Off. .
8806618 9/1988 PCT Int'l Appl. .

OTHER PUBLICATIONS

European Search Report for European Patent Application 91 11 2151.

Primary Examiner—Robert J. Warden
Assistant Examiner—T. A. Trembley
Attorney, Agent, or Firm—Ladas & Parry

[57] ABSTRACT

A plant tissue cutting and transplanting apparatus is provided with a supply system for plant receptacles which are covered by lids after plants that have been propagated and grown in a culture medium, a supply system for lidded empty receptacles that contain the culture medium, a lid opening and closing head to open and close the lids of the receptacles that are supplied by these supply systems, a square cutter to cut a predetermined number of plants in the receptacles that contain plants, and a transplanting head that is provided with a transplanting device to transplant these plant fragments that have been cut by the cutter from the square portions of the cutter to the culture medium in the empty receptacles. The transplanting device is provided with a plural number of pushing rods so as to correspond to the positions of the squares of the cutter, a plural number of lifting apparatus that can lift together each set of a predetermined number of these pushing rods, and a lifting apparatus that lifts the transplanting head.

1 Claim, 7 Drawing Sheets

PLANT TISSUE CUTTING AND TRANSPLANTING APPARATUS

BACKGROUND OF THE INVENTION

The present invention relates to a plant cutting and transplanting apparatus wherein a plant tissue has been cut to a certain size and automatically transplants it into a vessel when the cultivation of plant tissue is performed.

Many types of mass cultivation of plants is performed by cutting plant buds, shoots, roots, leaves, stems, flower petals and other plant tissue and transplanting the cut tissue to a culture medium where it is multiplied a fixed number of times.

Initially, the task of cutting the plant tissue was performed manually and the piece of the cut plant was transplanted to a culture vessel by hand, but there are several problems inherent to such manual processes. Such manual processes have the limit when cutting and transplanting have to be performed for a large number of plants. Therefore, it is not possible to meet requirements for mass cultivation, there is the great danger of contamination by microorganisms, and thus the work requires highly skilled persons.

Because of this, there has been proposed a system (U.S. Pat. No. 4910146 issued Mar. 20, 1990) wherein the plant tissue cutting and transplanting is performed by a mechanical means, the plant is cut by a cutter divided into squares (blocks), combinations of the selected squares are selected and compressed air is blown into the selected squares and the plant fragments that have adhered to the blades forming the squares of the cutter are blown onto the culture medium inside the receptacle and so that a constant interval between them is maintained.

However, in the propagation and transplanting apparatus disclosed above, the square plant fragments that are attached to the blades of the square cutter are placed on the culture medium by being blown by compressed air. Because of this, it is difficult to transplant the plant fragments at uniform intervals on the culture medium, and there is the additional problem which create an obstruction to growth due to existence of residues in the corners of the container. Furthermore, the plant fragments can easily be broken.

In the light of this, the present invention has as an object the provision of a plant tissue cutting and transplanting apparatus that can transplant the required number of plant fragments that have been cut to a square shape into an orderly and even arrangement.

SUMMARY OF THE INVENTION

In accordance with the present invention, a plant tissue cutting and transplanting apparatus is provided with a supply means for supplying plant receptacles which are covered by lids after plants that have been propagated and grown in a culture medium, a supply means for supplying lidded empty receptacles that contain the culture medium, a lid opening and closing head to open and close the lids of the receptacles that are supplied by these supply means, a square cutter to cut a predetermined number of plants in the receptacles that contain plants, and a transplanting head that is provided with a transplanting means to transplant these plant fragments that have been cut by the cutter from the square portions of the cutter to the culture medium in the empty receptacles. The transplanting means is provided with a plural number of pushing rods provided so as to correspond to the positions of the squares of the cutter, a plural number of lifting means that can lift together each set of a predetermined number of these pushing rods, and the lifting means that lifts the transplanting head.

Thus, lidded plant receptacles containing plants are propagated on the culture medium and lidded empty receptacles containing only culture medium are supplied by respective supply means, the lids of the both containers are opened by a lid opening means, and then the plant on the culture medium inside the containers is raised by the cutter as soon as the plant has been cut to the square shape, and the plant fragments that are affixed to inside the squares of the cutter are pressed by pushing rods onto the culture medium of the empty containers and thereby transplanted. At this time, the selection operation of the pushing rods enables the plant fragments to be transplanted into the receptacle so that a constant interval is maintained.

BRIEF DESCRIPTION OF THE DRAWINGS

FIG. 16 is a view of the underside of the transplanting head; and

FIG. 17 is a frontal elevational section through an empty receptacle.

DETAILED DESCRIPTION OF THE INVENTION

The following is a description of an embodiment of the present invention with reference to the appended drawings.

Figure 1:
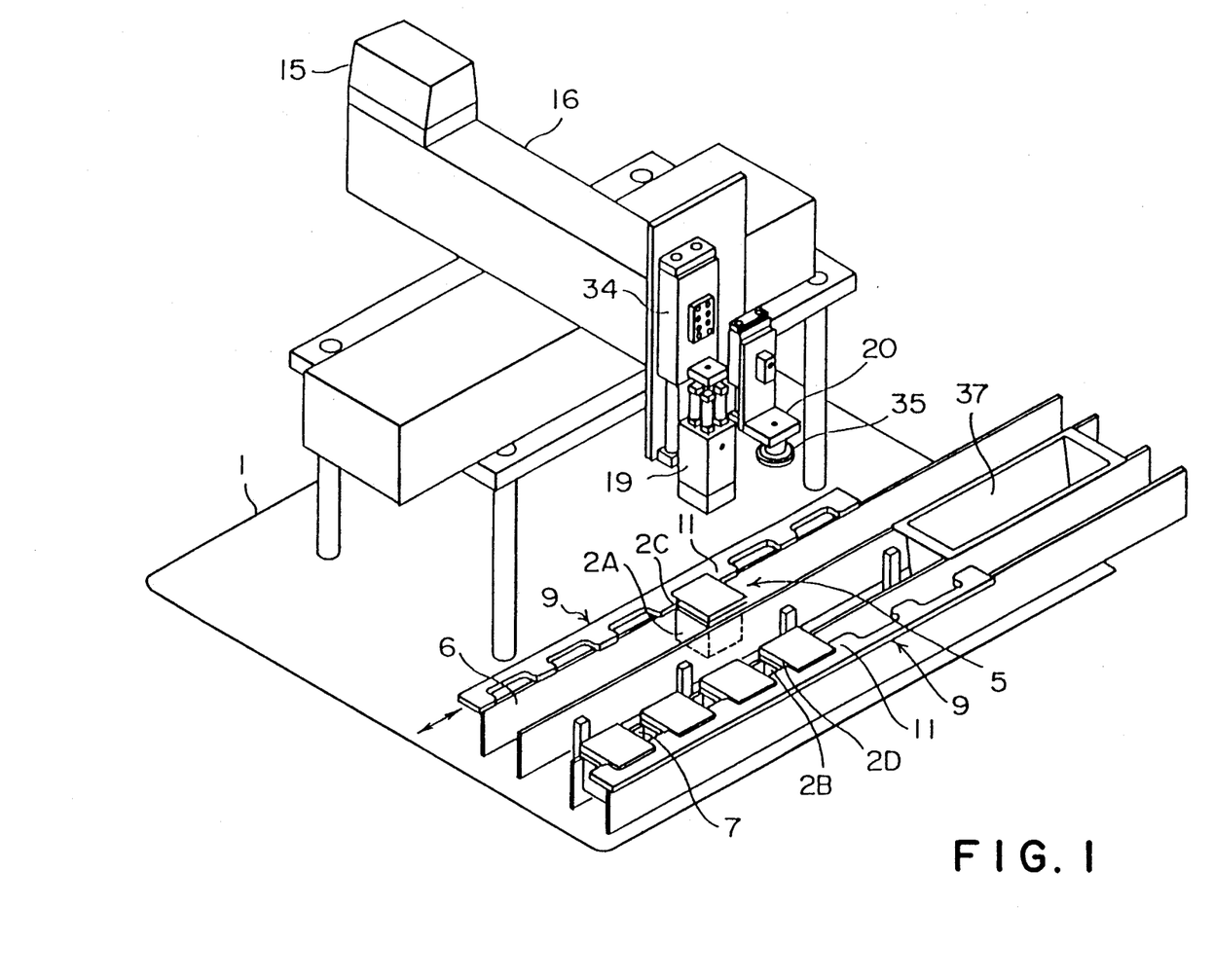
FIG. 1 is a perspective view indicating a plant tissue cutting and transplanting apparatus according to the present invention.
Figure 2:
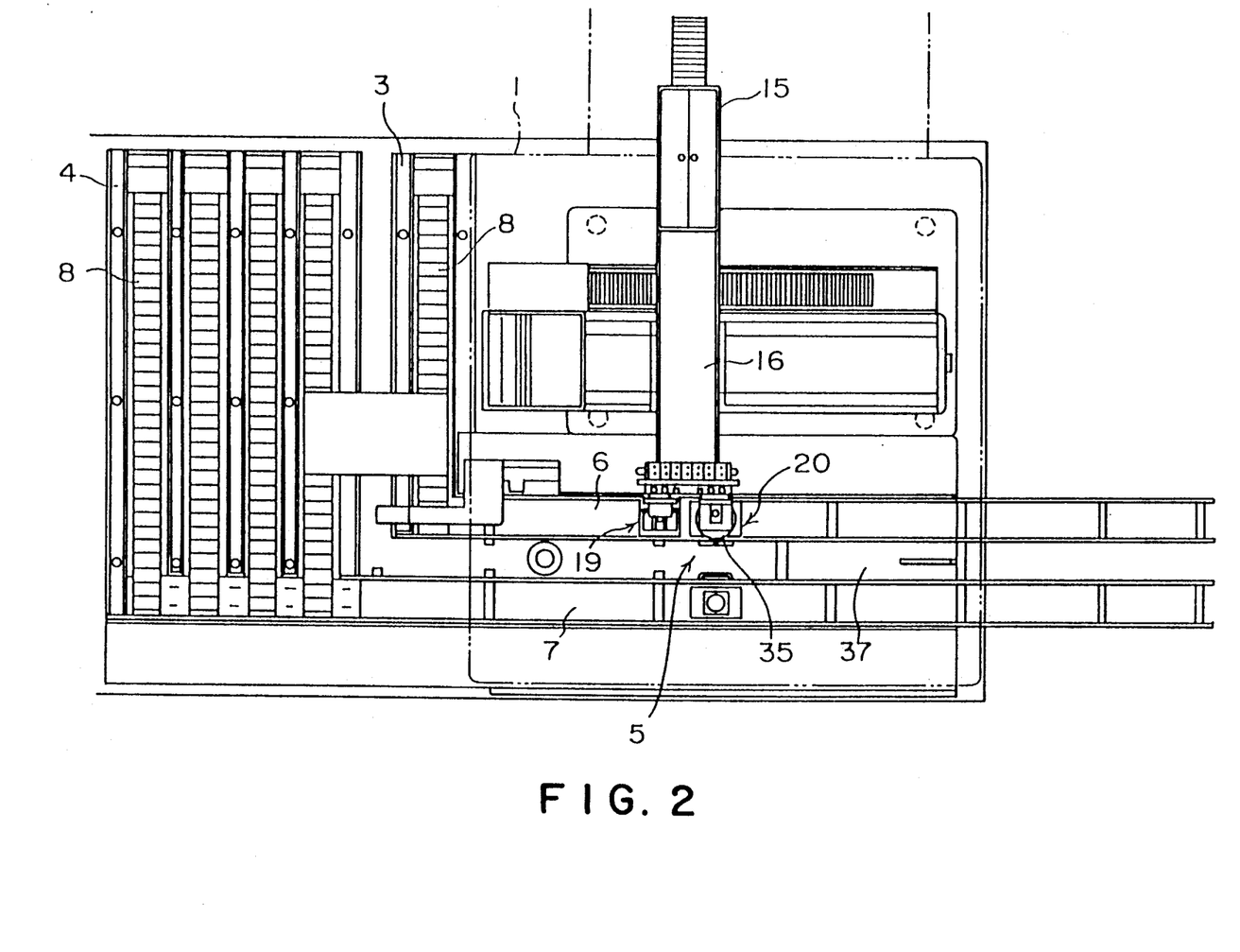
FIG. 2 is a plan view indicating the layout of the parts of the plant tissue cutting and transplanting apparatus of FIG. 1.
Figure 3:
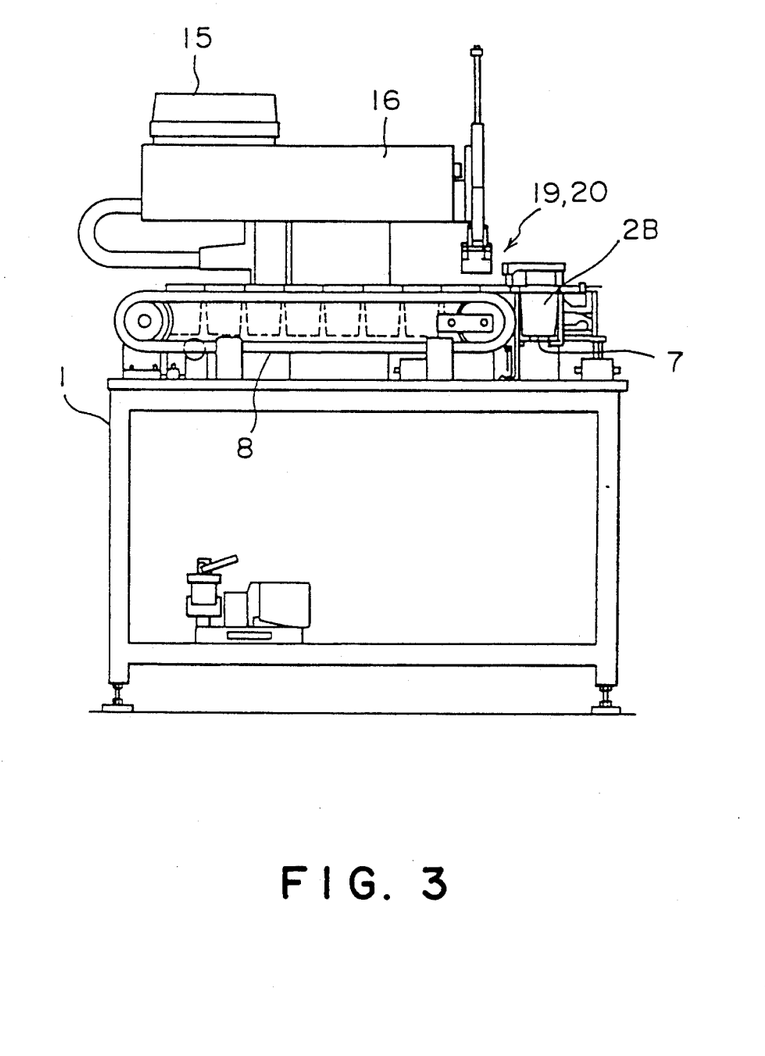
FIG. 3 is a left side elevational view.

In FIG. 1 and FIG. 2, a base 1 is provided with storage portions 3, 4 that respectively hold receptacles 2A (hereinafter called as "plant receptacles") containing plants that have been propagated on a culture medium inside them, receptacles 2B (hereinafter called as "empty receptacles") containing only the culture medium and which are to be used for transplanting, and a supply means for intermittently conveying these containers 2A, 2B along two linear conveyor paths 6, 7 in a line and at constant intervals from these storage portions 3, 4 to the cutting and transplanting portion 5.

In the embodiment shown in the drawing, the storage portions 3, 4 of the aforementioned supply means comprises plate conveyors 8 and conveyor paths 6, 7 that intersect at right angles at the ends of plate, conveyors 8. Receptacles 2A and 2B slide along storage portions the conveyors 6, 7 are provided with transfer means in order to convey the receptacles 2A and 2B at constant pitch and maintaining a constant interval between them.

Figure 4:
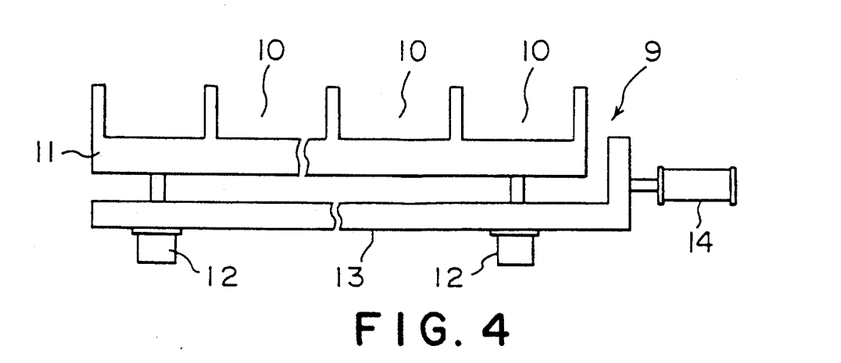
FIG. 4 is a partial cutaway plan view of the transfer means of FIG. 1.

Each of these transfer means 9 of which one has been omitted in FIG. 4, are as shown in FIG. 1, configured from a carrier 11 with C-shaped holders 10, that engage with the receptacles 2A, 2B and maintain them at a constant pitch a moving frame 13 that freely supports the rear of these carriers so that they can advance and retreat by cylinders 12, that move the carriers horizontally.

An operating cylinder 14 that is connected to end of this moving frame 13 and that moves the C-shaped holders backwards and forwards one at a time. Accordingly, when the carrier has advanced with respect to the moving frame 13, the receptacles 2A, 2B on the conveyor paths 6, 7 engage inside the C-shaped holders 10 and the movement of the moving frame 13 causes the carrier 11 to move in a rectangle so that the receptacles 2A, 2B are moved for a single pitch portion. However, this transfer means can be any other means as long as it sends the receptacles intermittently one pitch at a time.

An arm 16 of a robot 15 is provided with a transplanting head having a cutter 17 and a transplanting means 18, a lid opening and closing head 20 that opens and closes the lids 2C, 2D of the receptacles 2A, 2B, so that the both are provided at an interval corresponding to the conveyance pitch of the receptacles 2A, 2B.

In order to shorten the description, the cutter 17 of the transplanting head 19 and the transplanting means 18 are shown for the case where a plant in a plant receptacle 2A has been cut into $6 \times 6 = 36$ fragments and of these 36 pieces of plant fragments, 9 pieces are to be transplanted at a time as one set onto the culture medium 21 (shown in FIG. 14) inside one of the empty receptacles 2B.

Figures 7, 8:
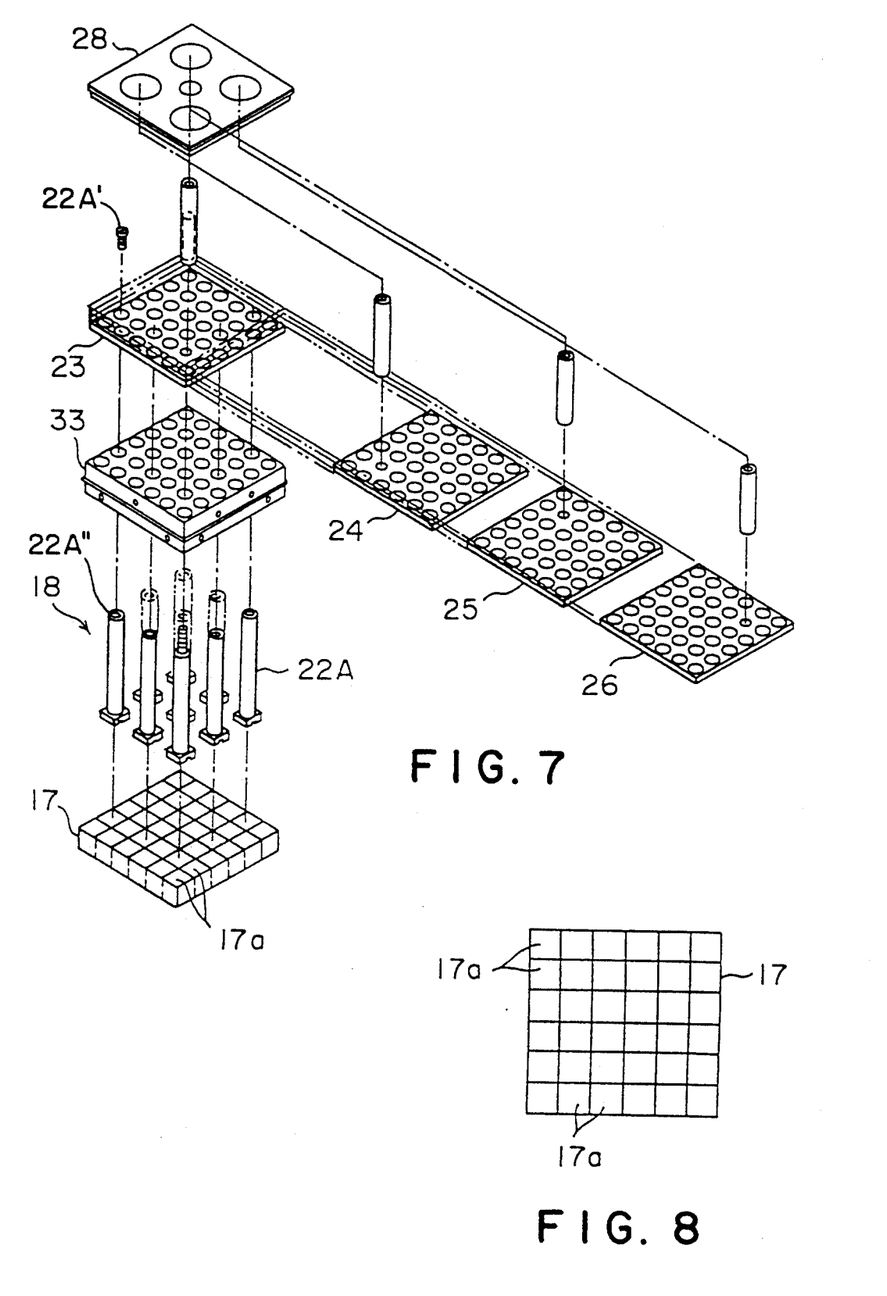
FIG. 7 is an exploded perspective view of the members configuring the transplanting head.
FIG. 8 is a plan view of the cutter.
Figure 9:
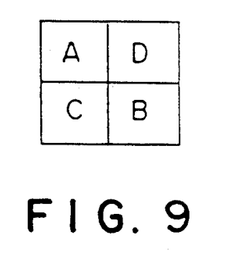
FIG. 9 is a view for describing the basic pattern of the cut plant fragments.
Figure 10:
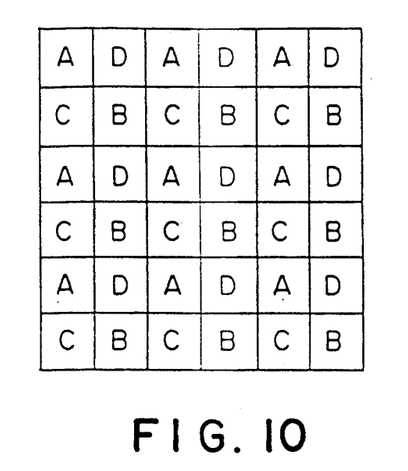
FIG. 10 is a view for describing the cutting pattern when there are nine fragments to a set.

The cutter 17 has an outer shape that can slides inside the receptacles 2A, 2B and as shown in FIG. 7 and FIG. 8, and has $6 \times 6 = 36$ squares 17 so that when the lower edges are blades 17b, then as shown in FIG. 9, the plant fragments are transplanted in accordance with the same pattern of arrangement of the four sets of squares A, B, C and D in FIG. 9 into the arrangement shown in FIG. 10.

The pushing rods 22 push the plant fragments that have been cut by the cutter 17 and which are affixed to and held inside the squares 17 and transplant them onto the culture medium 21 inside the empty receptacles 2B. The 36 pushing rods 22 have equal in number to the number of squares of the cutter 17 and the ends of these rods 22 are respectively provided with stamps 22' that can enter into one of the squares 17a of the cutter 17.

Figure 11:
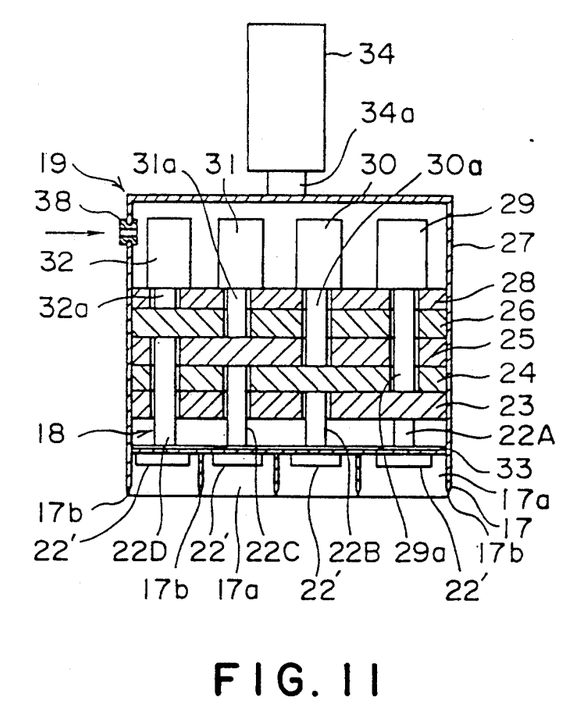
FIG. 11 is a sectional view indicating the basic principle of the transplanting means of the transplanting head.
Figures 12, 13:
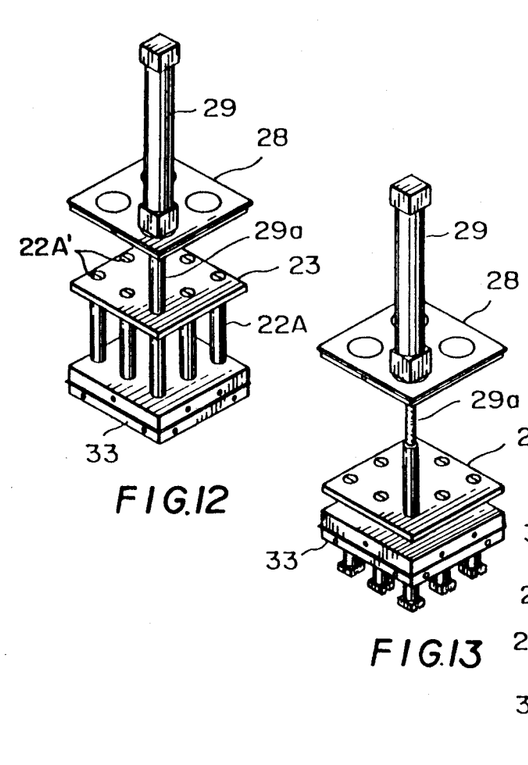
FIG. 12-15 are exploded perspective views of the transplanting head.

FIG. 11 indicates the principle of the configuration and as shown by the diagonally hatched portion in FIGS. 12-15 the 9 pushing rods 22A, that form the A set have their upper ends fixed to the bottom surface of a support plate 23, by means of screws 22A' which are screwed into thread holes 22A" formed on the ends of the pushing rods 22A, that fixes them in an arrangement corresponding to the positions of the A set squares, the 9 pushing rods 22B, that form the B set pass through the support plate 23 of the A set and have their upper ends fixed to the bottom surface of a support plate 24 that fixes them in an arrangement corresponding to the positions of the B set squares, the 9 pushing rods 22C, that form the C set pass through the support plates 23, 24 of the A, B sets and have their upper ends fixed to the bottom surface of a support plate 25 that fixes them in an arrangement corresponding to the positions of the C set squares, and the 9 pushing rods 22D, that form the D set pass through the support plates 23, 24, 25 of the A, B, C sets and have their upper ends fixed to the bottom surface of a support plate 26 that fixes them in an arrangement corresponding to the positions of the D set squares.

Each of these support plates 23, 24, 25, 26 are connected by rods 29a, 30a, 31a, 32a of cylinders 29, 30, 31, 32 positioned on a fixed base 28 of the casing 27, and function as a lifting means to lift each of the support plates 23, 24, 25, 26 individually. This is to say that the rods 29a of the cylinders 29 of the A set pass through the base 28 and the support plates 26, 25, 24 of the sets D, C, B and are connected to the support plates 23 of the A set, the rods 30a of the cylinders 30 of the B set pass through the base 28 and the support plates 26, 25 of the sets D, C and are connected to the support plates 24 of the B set, the rods 31a of the cylinders 31 of the C set pass through the fixed base 28 and the support plates 26 of the set D and are connected to the support plates 25 of the C set and the rods 32a of the cylinders 32 of the D set pass through the base 28 and are connected to the support plates 26 of the D set.

The base 33 that holds the cutter 17 from above is fixed to the lower end of the casing 27, and each of the support plates 23, 24, 25, 26 can move up and down freely inside the casing 27. The cylinders 29, 30, 31, 32 are fixed to the top of the base 28 above the casing 27. Furthermore, the casing 27 is connected to a rod 34a of a main cylinder 34 supported by an arm 16 of a robot 15.

In the arrangement described above, the squares A, B, C, D that form a square in themselves constitute one block as shown in FIG. 9, and if an integral multiple of these blocks are arranged in the X and Y directions then it is possible to increase or decrease the numbers of the same pattern. This is to say that the $6 \times 6 = 36$ blocks shown in FIG. 10 consist of the basic unit, but in addition, it is also possible to have $4 \times 4$ or $8 \times 8$ ... to give 16, 64, ...

The lid opening and closing head 20 is provided with respect to the transplanting head 19 so that it is at a spacing equivalent to a one conveyance pitch portion of the receptacles 2A, 2B on the conveyor paths 6, 7 and has a suction panel 35 provided to its lower surface so that this suction panel 35 sucks when it contacts the upper surface of the lids 2C, 2D of the receptacles 2A, 2B, and lifts the lids 2C, 2D in the upwards direction.

Between the conveyor paths 6, 7 at the side downstream from the cutting and transplanting head 5 is provided a cleaning tank 37 into which the cutter 17 is immersed, residual plant fragments are washed away, and which also sterilizes the cutter 17, and which is formed so that the lower end of the casing 27 can be immersed. The inside of the cleaning tank 37 is filled with an isopropyl alcohol as the cleaning liquid, but hot water or some other sterilizing agent can be used.

The upper side portion of the casing 27 is provided with air supply nozzles 38 in order to mainly dry the insides of the cutter squares and blow away residues of the plant fragments therefrom, and the portions inside the casing, and after the transplanting operation, air is discharged downwards from these nozzles 38 to perform drying and blowing away. Moreover, in order to improve the air flow, cutouts 22a are formed in one corner of each of the stamps 22' as shown in FIG. 16.

Figure 5:
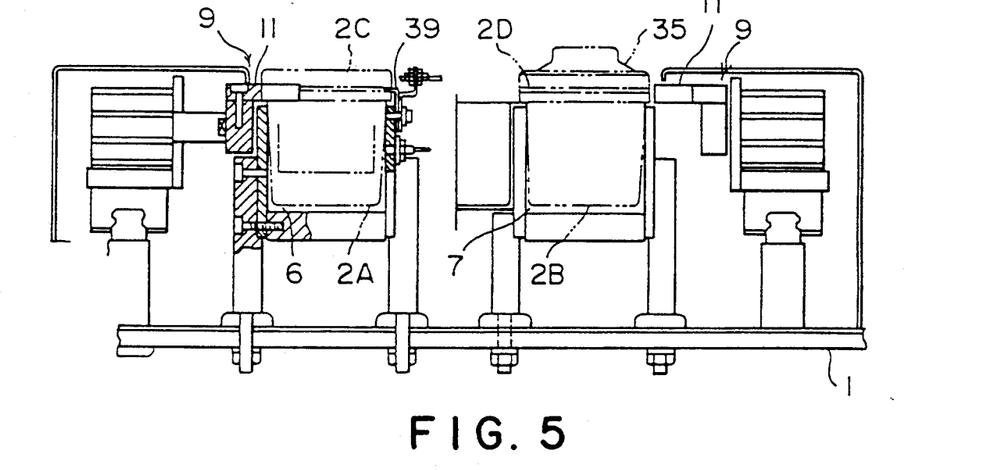
FIG. 5 is a sectional front elevational view of one portion of the conveyor path of the cutting and transplanting portion.
Figure 6:
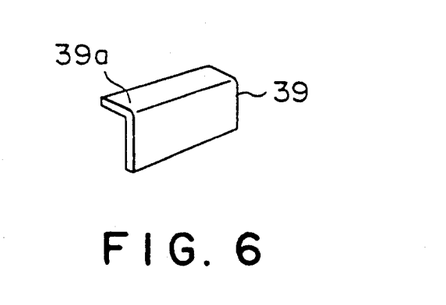
FIG. 6 is a perspective view of the lid lifting portion in FIG. 5.

In the transplanting head 5, an inverted L-shaped lid lifting portion 39 is provided as shown in FIG. 6, to one side of the conveyor paths 6, 7 as shown in FIG. 5, so as to facilitate the removal of the lids 2C, 2D of the containers 2A, 2B, and the horizontal portion 39a of this inverted L-shaped lid lifting portion 39 enters between the lower edge of the lids 2C, 2D and the edge of the mouth of the receptacles 2A, 2B that pass, and lifts the lids 2C, 2D upwards slightly so that the lids can be opened definitely.

The following is a description of the operation of the embodiment described above.

Plant receptacles having plant tissues therein are lined on the plate conveyor 8 of the storage portion 3, and empty receptacles 2B containing on culture medium 21 are lined on the plate conveyor 8 of the storage portion 4, respectively.

The receptacles 2A, 2B are conveyed from the end of the plate conveyors 8 to the conveyor paths 6, 7 and the receptacles 2A, 2B on the conveyor paths 6, 7 are intermittently fed one at a time by the transfer means 9 and at a constant pitch.

At the position of the cutting and transplanting portion 5, the lid opening and closing head 20 of the robot 15 takes the lid 2C from the receptacle 2A and places it on the receptacle in front of it. Then, when that receptacle 2A is positioned beneath the transplanting head 19, the transplanting head 19 lowers due to the action of the main cylinder 34 and the cutter 17 enters into the receptacle 2A and cuts the plant tissue therein into squares.

After this, the transplanting head 19 rises and covers the receptacle 2A with the lid 2C. Then, the transplanting head 19 moves to above the empty receptacle 2B and takes the lid 2D, the transplanting head 19 lowers and enters into the receptacle. In this example, the cylinders 29 of set A operate, lowers the support plate 23, and lower the 9 pushing rods 22A, that are supported by the supporting plate 23, and the plant fragments that are affixed inside the cutter squares 17 of the cutter 17 and which correspond to those rods are pushed downwards and out from inside the cutter squares 17a and are transplanted to on the culture medium 21 inside the receptacle 2B (Refer to FIG. 12→FIG. 13.

Figure 14:
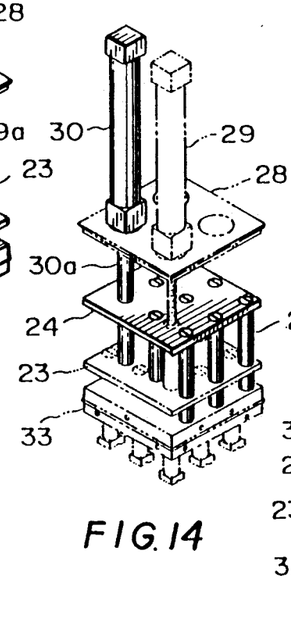
Figure 15:
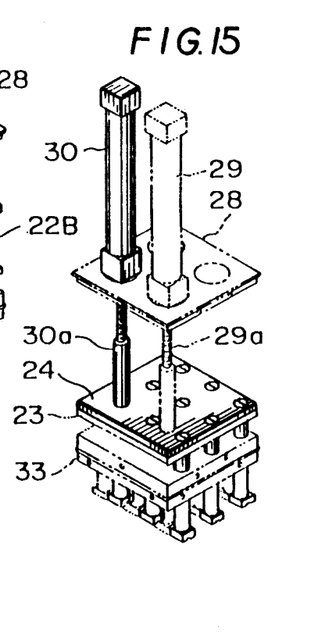

When the transplanting of the plant fragments of set A has been completed, the transplanting head 19 rises and the row of empty receptacles 2B is advanced one pitch portion by the transfer means 9, and the next empty receptacle 2B is positioned under the transplanting head 19. Here, the transplanting head 19 lowers once again and the cylinders 30 of the set B operate to lower the support plate 24, and lower the 9 pushing rods 22B, that are supported by that supporting plate 24, and the plant fragments that are affixed inside the cutter squares 17a of the cutter 17 and which correspond to those rods are pushed downwards and out from inside the cutter squares 17a (Refer to FOG/ 14→FIG. 15.

In this manner, the plant fragments of set C and set D are respectively transplanted to inside the empty receptacles 2B.

When the transplanting of sets A through D has been completed, the action of the robot 15 immerses the transplanting head 19 inside the cleaning tank 37 and residual plant matter is washed off and sterilization processing performed, the transplanting head 19 lifted out and the inside thereof dried by air blown from an air supply nozzle 38.

During this time, the plant receptacles 2A are advanced a one pitch portion by the transfer means 9 to the predetermined position of the cutting and transplanting means 5, the lid 2C is taken off and operation the same as has already been described is repeated to perform the transplanting to inside the empty receptacles 2B.

Moreover, in the embodiment shown in the FIGURE, the plate conveyors 8, are shown as the means to send the two types of receptacles 2A, 2B from the storage portions 3, 4 but pushers can be used to send either one or a row of receptacles at a time. In addition, it is preferable that the robot 15 have two or three axes at right angles but this can be replaced with a combination of air cylinders, plungers and pinions and a link mechanism and the like. Instead of a suction panel 35, the holding of the lids 2C, 2D of the lid opening and closing head 20 can alternatively be performed by a clip or sliding type of holding fitting, and depending upon the size of the cut, when it is difficult for the plant fragments inside the squares 17a of the cutter 17 to be held by self-affixing alone, it is possible to use a negative pressure inside the squares. In this case, it is desirable that the suction be controlled for each set.

According to the present invention as has been described above, when a large number of plants have been propagated and are transplanted to on a culture medium in a receptacle, the transplanting is performed by the pushing action of the pushing rods of each square set and so it is possible to transplant in regular arrangements without scattering on the culture medium inside the receptacle even after the plants have been cut, and therefore achieve the favorable propagation from plant fragments.

While the above description constitutes the preferred embodiments of the present invention, it will be appreciated that the invention is susceptible to modification, variation and change without departing from the proper scope and fair meaning of the accompanying claims.

What is claimed is:

1. A plant tissue cutting and transplanting apparatus comprising:
   a lid opening head for opening a lid of a first receptacle containing a plant tissue;
   a first supply means for feeding said first receptacle to said lid opening head;
   a square cutter for cutting said plant tissue in said open first receptacle into a number of plant fragments in a pattern of at least four sets of squares;
   transplanting means for transplanting said number of plant fragments from said square cutter to culture medium in empty receptacles;
   first lifting means for lifting said transplanting means; and
   a second supply means for feeding said empty receptacles to said transplanting means;
   said transplanting means comprising a plurality of pushing rods in sets respectively corresponding to said four sets of squares from said square cutter and second lifting means for respectively lifting together said sets of said plurality of pushing rods,
   wherein a first set of said sets of said plurality of pushing rods for a first set of said sets of squares has upper ends fixed to a bottom surface of a first support plate which fixes said first set of said plurality of pushing rods in an arrangement corresponding to said first set of squares, a second set of said sets of said plural of pushing rods for a second set of said sets of squares passes through said first support plate and has upper ends fixed to a bottom surface of second support plate which fixes said second set of said plurality of pushing rods in an arrangement corresponding to said second set of squares, a third set of said sets of said plurality of pushing rods for a third set of said sets of squares passes through said first and second support plates and has upper ends fixed to a bottom surface of a third support plate which fixes third set of said plurality of pushing rods in an arrangement corresponding to said third set of squares, and a fourth set of said sets of said plurality of pushing rods for a fourth set of said sets of squares passes through said first, second and third support plates and has upper ends fixed to a bottom surface of a fourth support plate which fixes said plurality of pushing rods in an arrangement corresponding to said fourth set of squares, and wherein cylinders are mounted on a fixed base of a casing, a rod of a first cylinder of said cylinders for said first set of said sets of said plurality of pushing rods passes through said fixed base and said second, third and fourth support plates and is connected to said first support plate, a rod of a second cylinder of said cylinders for said second set of said sets of said plurality of pushing rods passes through said fixed base and said third and fourth support plates and is connected to said second support plate, a rod of a third cylinder of said cylinders for said third set of said sets of said plurality of pushing rods passes through said fixed base and said fourth support plate and is connected to said third support plate, and a rod of a fourth cylinder of said cylinders for said fourth set of said sets of said plurality of pushing rods passes through said fixed base and is connected to said fourth support plate, whereby each of said support plates is moved individually in said casing by means of said cylinders.

* * * * *